United States Patent [19]
Aboud

[11] Patent Number: 5,338,290
[45] Date of Patent: Aug. 16, 1994

[54] ELASTIC VARIABLE TENSION DEVICE FOR THE TREATING OF PAIN

[76] Inventor: George M. Aboud, 3939 E. Glenrosa, Phoenix, Ariz. 85018

[21] Appl. No.: 96,593

[22] Filed: Jul. 21, 1993

[51] Int. Cl.⁵ .............................................. A61F 13/00
[52] U.S. Cl. ..................................... 602/75; 606/201; 606/204; 602/74; 602/62
[58] Field of Search ..................... 602/75, 60, 62, 64, 602/65, 74, 61, 77; 606/201, 204, 203; 273/188 R, 189 R

[56] References Cited

U.S. PATENT DOCUMENTS

| | | |
|---|---|---|
| 3,598,114 | 8/1971 | Lewis . |
| 3,710,790 | 1/1973 | Lemon . |
| 3,880,161 | 4/1975 | Fossel . |
| 3,886,939 | 6/1975 | Boxer . |
| 3,915,163 | 10/1975 | Sakamura . |
| 3,926,186 | 12/1975 | Nirschl . |
| 3,942,525 | 3/1976 | Dragan . |
| 4,128,097 | 12/1978 | Bilinsky et al. . |
| 4,215,687 | 8/1980 | Shaw . |
| 4,243,028 | 1/1981 | Puyana . |
| 4,273,130 | 6/1981 | Simpson . |
| 4,299,214 | 11/1981 | Sweitzer . |
| 4,369,775 | 1/1983 | Gamm . |
| 4,505,271 | 3/1985 | Weber . |
| 4,693,241 | 9/1987 | Trznadel . |
| 4,734,320 | 3/1988 | Ohira et al. . |
| 5,137,508 | 8/1992 | Engman ............... 602/61 X |
| 5,152,302 | 10/1992 | Fareed . |

Primary Examiner—Richard J. Apley
Assistant Examiner—Beverly A. Meindl
Attorney, Agent, or Firm—Ogram & Teplitz

[57] ABSTRACT

The invention creates an elastic variable tension medical device that relieves pain due to injury, disease, ailment, infirmity, condition, or the like. The elastic variable tension medical device is comprised of multiple strips of elastic material stacked one on top of another and forming a stack of elastic strips. Hook and loop fasteners are attached to each end of the elastic variable tension medical device for securing the elastic variable tension medical device around a part of the body. Reinforcing ribs on the elastic variable tension medical device provide increased strength and reduce folding and binding of the elastic material. The elastic variable tension medical device is wrapped around an appropriate part of the body with sufficient tension to relieve the targeted pain. It is adjusted by the user to achieve the desired pain relief.

15 Claims, 5 Drawing Sheets

ELASTIC VARIABLE TENSION DEVICE FOR THE TREATING OF PAIN

BACKGROUND OF INVENTION

This invention relates generally to medical apparatus and more specifically to devices for relieving pain due to medical conditions, injuries, ailments, infirmities, or the like.

Millions of people suffer from pain everyday due to conditions such as injured tendons, ligaments and muscles, sprained or twisted joints, arthritis, headaches, tendinitis, tennis elbow, carpal tunnel syndrome, and other painful ailments. Many of these ailments have no treatment but to block the pain until the condition heals itself.

There are two major methods of treating pain. One method uses drugs, taken either orally or by injection, to block or deaden the pain. The second method uses some sort of physical therapy to eliminate the source of the pain or to block the pain.

Because of the many perceived disadvantages of drugs and the advantages of physical therapies, more and more people are turning to physical therapies to relieve their pain. These alternative physical therapies include chiropractic care, massage therapy, acupressure, acupuncture, hand and foot reflexology, muscle therapy, and other physical therapies. The advantages of these therapies include reduced cost, home treatment, self treatment, and sometimes, improved result.

Many devices existing to relief pain use the concepts of physical therapy. However, most of these devices have drawbacks which limit their effectiveness.

One class of devices which are sometimes used to relieve pain are sports type elastic bandages. These bandages typically consist of a long strip of stretch material with metal fasteners for securing the stretch material to itself. A sports type elastic bandage is wrapped snugly around an injury, such as a knee or elbow, to support the ligaments, tendons, or muscles. They are also used to support sprains, strains, and to provide support during strenuous activities.

Sports type elastic bandages have several disadvantages. They are not easily adjustable since they must be unwrapped and re-wrapped to adjust the tension. Second, the metal fasteners can be uncomfortable. Third, sports type elastic bandages can bind and gouge into a person's body. Finally, they are not designed specifically to block pain. Sports type elastic bandages are primarily designed for supporting an injury to promote healing of the injury and therefore are not effective at blocking pain. The reason that they do not block pain is that sufficient tension is lacking to achieve pain relief; also, the width of the bandage is excessive for localized tension.

These types of bandages are available commercially from several sources. ACE ® brand sports bandages are available from Becton Dickinson & Company, Franklin Lakes, N.J. SELFGRIP ® brand sports bandages are available from LMA, Ltd., S. Norwalk, Conn.

Another type of bandage device is known as a rib belt. Rib belts are designed for supporting injured ribs. These devices use a wide strip of elastic material which is wrapped around a patent's rib cage and fastened to itself with hook and loop type fasteners.

Rib belts are too big for many applications. Further, the device tends to fold and cut into a user making it very uncomfortable. Finally, the material and construction used in rib belts make them too weak to work well as a pain blocking device.

One brand of rib belts is available from Acorn Development Cos., Inc., Newark, N.J. and is known by the Trademark CAREX ®.

Both sports bandages and the rib belts primarily provide support and protection for an injury, thus allowing the injury to heal. They may also avert further injury or pain by immobilizing and protecting the injured area. They are not designed nor are they intended to function primarily as a pain relieving device.

Support gloves are yet another device known in the art. Support gloves fit snugly over the hand and are often made of elastic material. These gloves provide some pain relief from pain in the hands, however, they are too weak and provide too little support to be completely effective. In addition, these gloves make it virtually impossible to use the hand in a work situation and cannot be readily laundered.

There continues to be a need for a device which provides effective pain relief without the use of drugs or other expensive treatments and is easily self administered.

Clearly, there exists a need for a medical device which relieves pain, is simple and inexpensive, can be self administered, and uses no drugs.

SUMMARY OF THE INVENTION

The invention creates an elastic variable tension medical device that relieves pain due to injury, disease, ailment, infirmity, condition, or the like.

The elastic variable tension medical device is comprised of multiple strips of elastic material stacked one on top of another and forming a stack of elastic strips. Hook and loop fasteners are attached to each end of the elastic variable tension medical device for securing the elastic variable tension medical device around a part of the body. Reinforcing ribs on the elastic variable tension medical device provide increased strength and reduce folding and binding of the elastic material.

The elastic variable tension medical device is wrapped around an appropriate part of the body with sufficient tension to relieve the targeted pain. It is adjusted by the user to achieve the desired pain relief.

It has been found that when a bandage of adequate size and strength is wrapped with sufficient tension to relieve pain around a body part, pain from a related body area is relieved or blocked. It is believed that this phenomena is related to the techniques of acupressure, hand and foot reflexology, muscle therapy, and the like which are still not completely understood to science. These techniques are discussed in the following books which are all hereby incorporated by reference:

"SHIATSU, Japanese Finger Pressure Therapy", by William Shultz, Published by Bell Publishing Company, 1976;

"HEALING MASSAGE TECHNIQUES, Holistic, Classic, and Emerging Methods", Second edition, by Frances Tappan, Published by Appleton & Lange, 1988;

"How to Heal Yourself Using Hand Acupressure (Hand Reflexology)", by Michael Blate, Published by Falkynor Books, 1982; and, "MYOTHERAPY, Bonnie Prudden's Complete 'guide To Pain-Free Living", by Bonnie Prudden, Published by The Dial Press, 1984.

The current invention is specifically designed to utilize this discovery for the relief of pain.

The elastic variable tension medical device is comprised of at least one strip of elastic material. Strips of elastic material of equal size are stacked one on top of another. The length and width of the strips of elastic material is dependent on the target area of the body where the elastic variable tension medical device will be applied. An elastic variable tension medical device for use on a wrist is necessarily shorter than one for use on the upper arm or thigh.

Multiple strips of elastic material add strength to the elastic variable tension medical device. The number of strips of elastic material used is dependent on the particular application, however, the preferred embodiments use two or three strips of elastic material.

The elastic variable tension medical device is wrapped around a body part and secured to itself using the overlapping hook and loop fasteners. The hook and loop fasteners permit easy application and removal of the device. They also allow the device to be easily adjusted by the user to the tension desired by the user.

Reinforcing ribs are used to enhance the effectiveness of the elastic variable tension medical device. Reinforcing ribs attach the strips of elastic material together and extend across the width of the elastic variable tension medical device. The reinforcing ribs add strength and firmness to the elastic variable tension medical device. They also deter the strips of elastic material from folding and consequently digging into the user. This type of construction maintains the elastic qualities of the device while furnishing a comfortable fit.

In the preferred embodiment, the reinforcing ribs are constructed by stitching the strips of elastic material together in a line extending across the width of the elastic variable tension medical device.

It has been found that application of the elastic variable tension medical device to an appropriate location on the body and with sufficient tension, releases the sensation of pain from an injury.

The elastic variable tension medical device is wrapped about an appropriate part of the body with sufficient tension to relieve pain. For example, to block pain in an elbow, the elastic variable tension medical device is preferably wrapped around the forearm one or two inches below the elbow. Likewise, pain in a knee is relieved by wrapping the elastic variable tension medical device around the leg just below the knee. In general, joint pain is reduced by wrapping the elastic variable tension device around a portion of the body at least one inch distal to the joint. Pain from a hamstring is relieved by wrapping the elastic variable tension medical device around the thigh above the pain in the hamstring. The elastic variable tension medical device is adjusted by the user so that it is just tight enough to block the pain. The user easily adjusts the tension and position of the elastic variable tension medical device to control the pain as needed.

The significant features of the invention are illustrated in the figures and described more fully below.

DETAILED DESCRIPTION OF THE DRAWINGS

Figure 1:
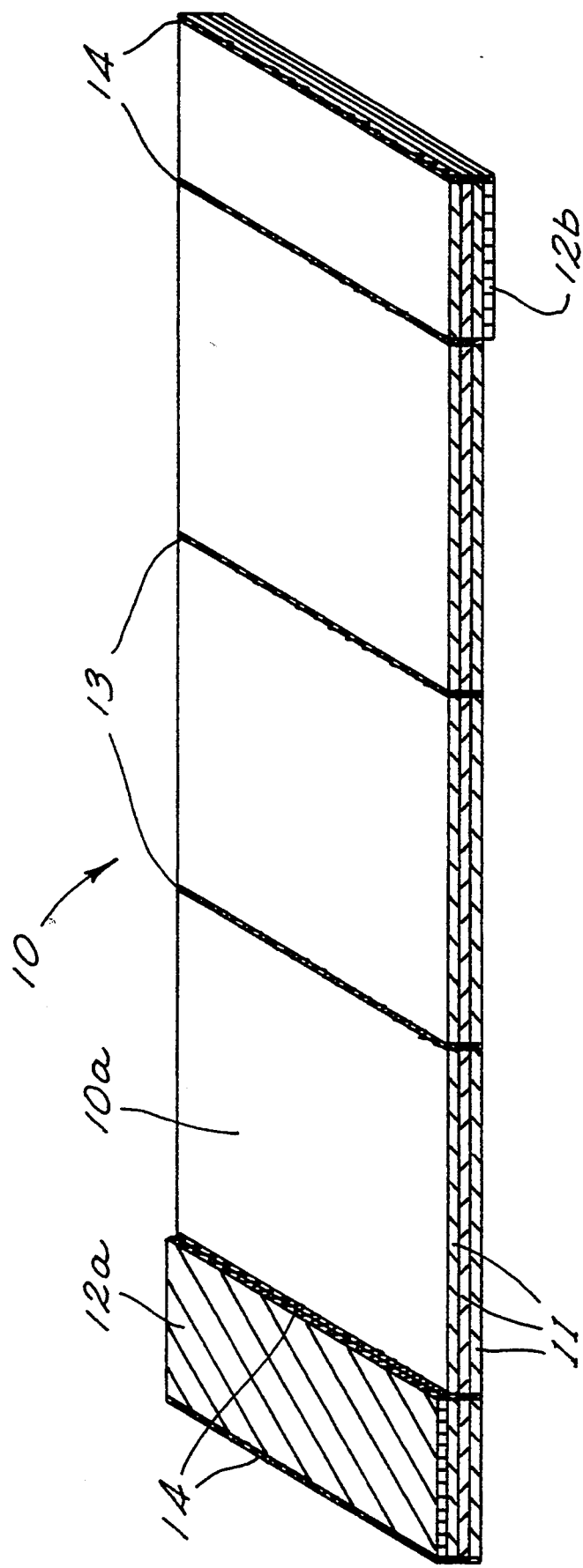
FIG. 1 is a perspective view of the preferred embodiment of the invention.

FIG. 1 is a perspective view of the preferred embodiment of the invention.

Elastic variable tension medical device 10 is comprised of three strips of elastic material 11, hook and loop fastener 12 having a hook portion 12a and a loop portion 12b, and reinforcing ribs 13.

Strips of elastic material 11 are made of any elastic material. The preferred embodiment uses elastic material that is porous and breathable and therefore permits moisture to vent. The length and width of the elastic variable tension medical device 10 is dependent on the intended application. In the preferred embodiments, the elastic variable tension medical devices 10 are from one to six inches wide.

Hook and loop fastener 12 is attached to the ends of elastic variable tension medical device 10. The hook portion 12a of hook and loop fastener 12 is attached to a first end of the elastic variable tension medical device 10 and on a first side 10a of elastic variable tension medical device 10. The loop portion 12b of hook and loop fastener 12 is attached to a second end of the elastic variable tension medical device 10 and on a second side (not shown) of elastic variable tension medical device 10.

Hook and loop fastener 12 is preferably stitched to the strips of elastic material 11 with stitching 14. Stitching 14 also provides reinforcement and support in the same manner as reinforcing ribs 13.

When elastic variable tension medical device 10 is wrapped around a body part, hook portion 12a and loop portion 12b overlap and attach to one another. Hook and loop fastener 12 allows a wide range of adjustments. Elastic variable tension medical device 10 is easily loosened or tightened as desired.

Hook and loop fasteners are commonly known in the art. One brand of hook and loop fasteners is known by the trademark VELCRO ®.

Reinforcing ribs 13 add strength and support to elastic strips 11. Reinforcing ribs 13 attach all of the elastic strips 11 together along the span of reinforcing ribs 13.

Stitching is preferably used to create reinforcing ribs 13. Stitching provides the necessary strength and support without the need for rigid reinforcing means. Other flexible reinforcing means are also envisioned including, but not limited to, gluing, stapling, and other flexible fastening means commonly known in the art.

Figure 2:
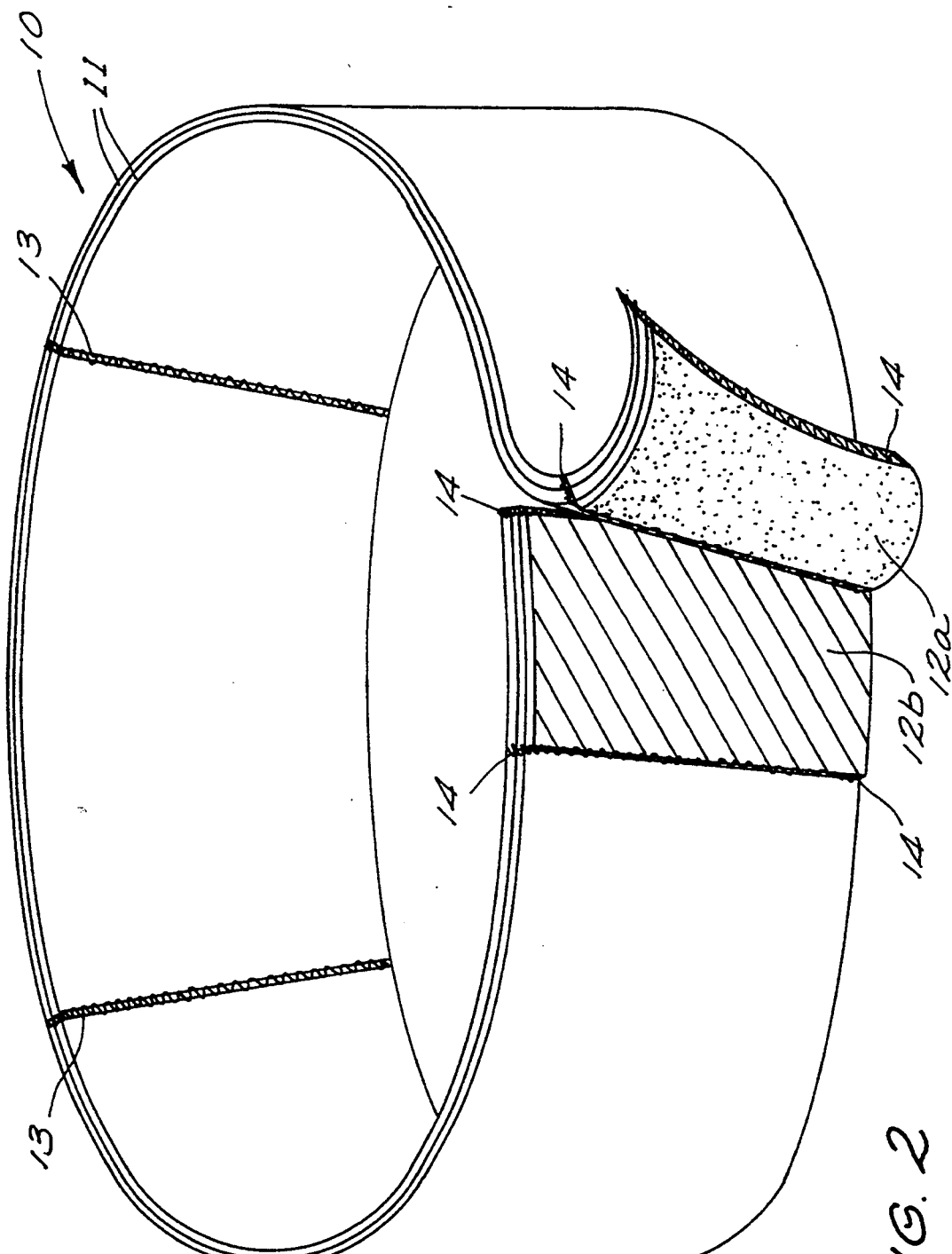
FIG. 2 shows the invention wrapped around and attached with the hook and loop fastener.

FIG. 2 shows the elastic variable tension medical device 10 wrapped around and attached to itself by hook and loop fastener 12. Hook portion 12a of hook and loop fastener 12 attaches to loop portion 12b of hook and loop fastener 12. Hook and loop fastener 12 is attached to elastic strips 11 by stitching 14. Stitching 14 also provides reinforcement and support in the same manner as reinforcing ribs 13. Reinforcing ribs 13 attach the elastic strips 11 together and provide reinforcement, support, and increased lateral strength for the elastic variable tension medical device 10.

FIGS. 3a thru 3d show several applications of the invention.

Figure 3A:
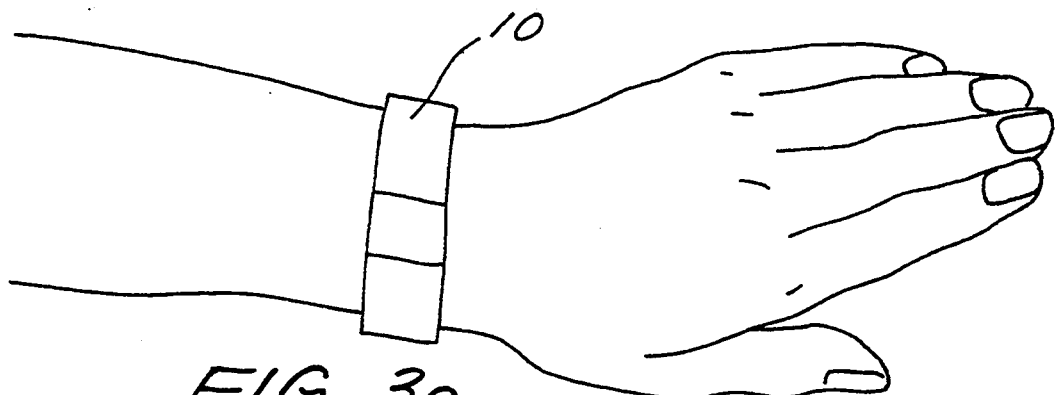
FIG. 3a shows the application of the invention for relieving pain in the hand or wrist.

FIG. 3a shows the elastic variable tension medical device 10 applied just proximal to the wrist of the hand. In this position, the invention is useful in relieving pain from the wrist and hand. The invention relieves pain caused by the painful condition known as carpal tunnel syndrome and other painful conditions of the wrist and hand.

Figure 3B:
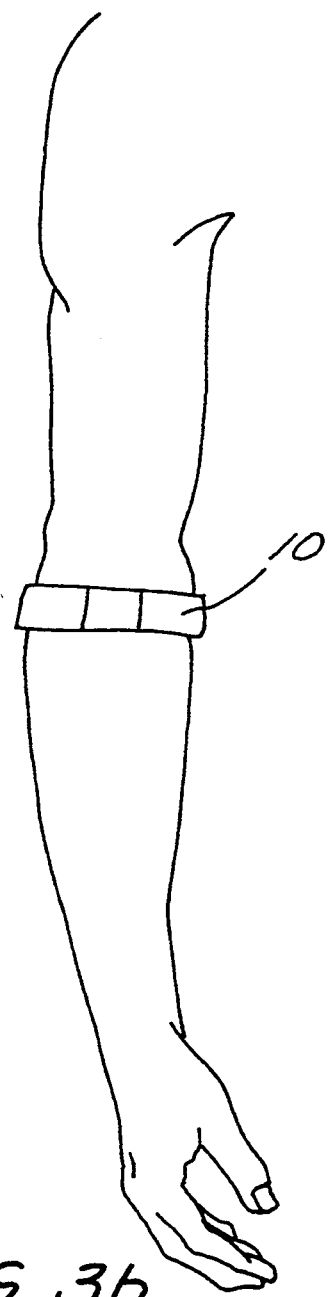
FIG. 3b shows the invention used to relieve pain in the elbow and forearm.

FIG. 3b shows the elastic variable tension medical device 10 applied around the lower arm distal to the elbow. This position is useful to relieve pain in the elbow. The invention is effective in relieving pain from epicondylalgia (tennis elbow) and other painful conditions of the elbow.

Figure 3C:
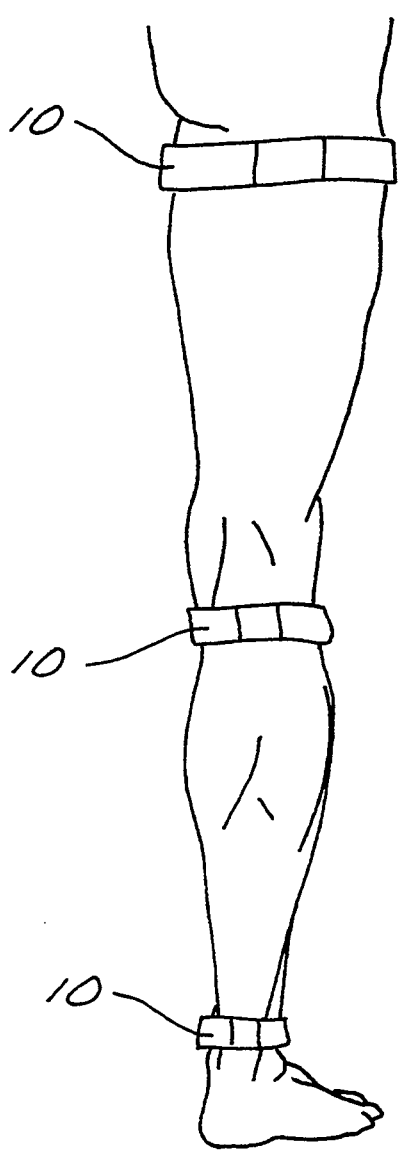
FIG. 3c shows the invention used to relieve pain in the ankle, knee or thigh (hamstring).

FIG. 3c shows the elastic variable tension medical device 10 applied around the ankle, around the leg just distal to the knee and around the upper thigh. The invention 20 applied around the ankle relieves pain in the ankle. The invention 20 applied just below to the knee relieves pain in the knee and lower leg. The preferred application is two inches below the knee. The elastic variable tension medical device 10 is also applied near the top of the thigh. In this position the invention relieves pain in the thigh including pulled or injured hamstrings and the like.

Figure 3D:
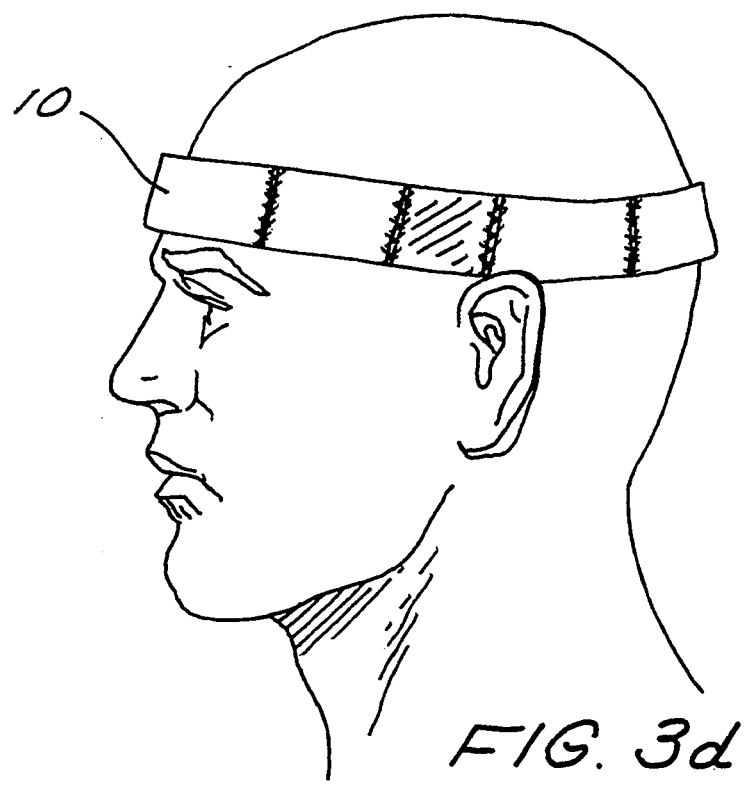
FIG. 3d shows the invention used to relieve headache pain.
Figure 4A:
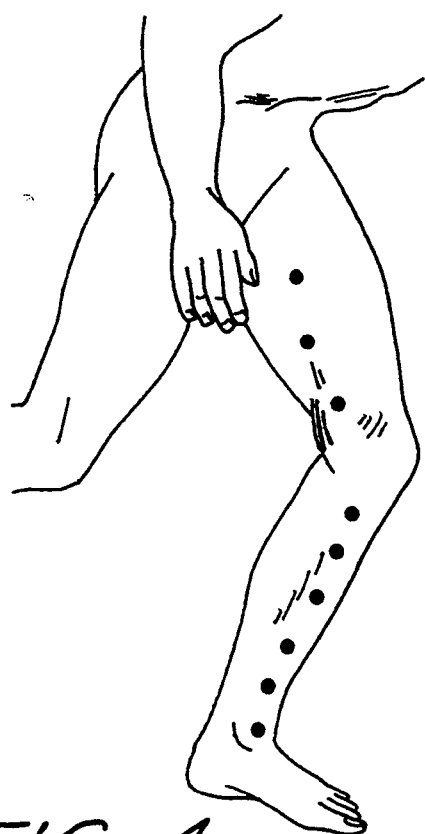
FIG. 4A shows pressure points on the leg.
Figure 4B:
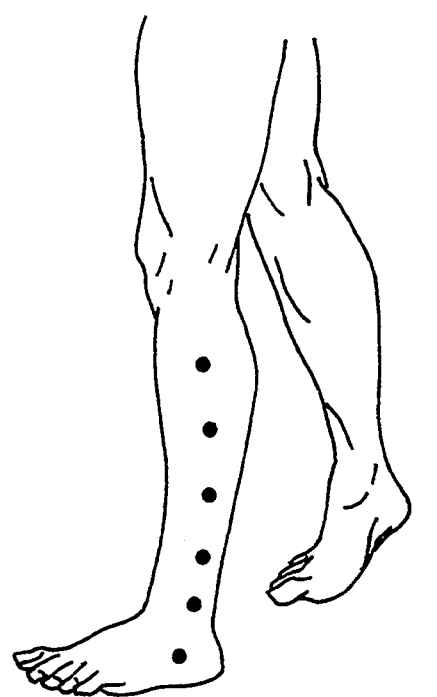
FIG. 4B shows pressure points on the outside of the calf.
Figure 4C:
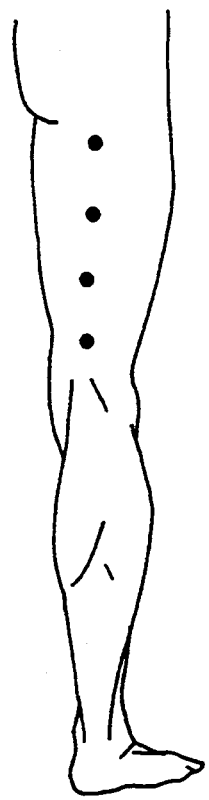
FIG. 4C shows pressure points on the back of the thigh.
Figure 4D:
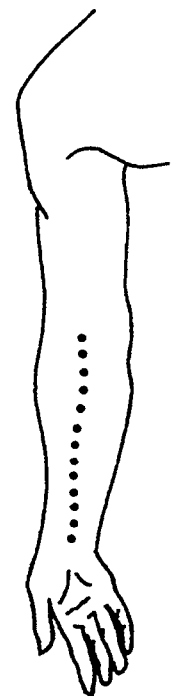
FIG. 4D shows pressure points on the arm.
Figure 4E:
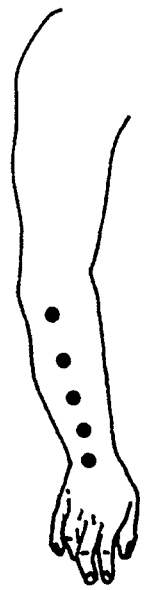
FIG. 4E shows pressure points on the forearm.
Figure 4F:
FIG. 4F shows pressure points on the upper arm.
Figure 4G:
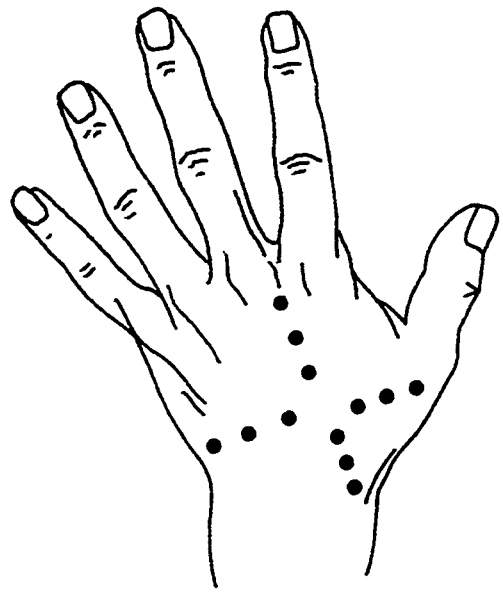
FIG. 4G shows pressure points on the hand.

FIG. 3d shows the elastic variable tension medical device 10 applied around the head and particularly the temples of a patient. This position is useful in relieving various headaches, sinus aches, and the like.

FIGS. 4A through 4G show various pressure points to which the invention is applied.

It is understood that this represents merely a sampling of the uses and applications of the invention. A great many pressure points exist on the body and, consequently, a great many positions for the invention are envisioned.

Those of ordinary skill in the art readily see many alternate embodiments of the disclosed invention which perform substantially the same function or work, in substantially the same way, to obtain substantially the same overall result and would therefore infringe on the disclosed invention.

It is clear from the foregoing that the present invention represents a new and useful device for relieving pain without the side effects of drugs, therapies, or other expensive medical treatments.

What is claimed is:

1. An elastic variable tension medical device comprising:
   a) an elastic band stack having at least two elastic bands stacked one atop another and forming a stack of elastic bands, said stack of elastic bands having a first end and a second end and having a first side and a second side, said at least two elastic bands being attached to one another at said first end and at said second end;
   b) a hook and loop fastener having,
      1) a hook portion attached to said first end of said elastic band stack and on said first side of said elastic band stack, and,
      2) a loop portion attached to said second end of said elastic band stack and on said second side of said elastic band stack; and,
   c) at least one reinforcing rib, said at least one reinforcing rib attached to said stack of elastic bands between said first end and said second end and extending across the width of said stack of elastic bands, and wherein each of said at least one reinforcing ribs is a series of stitches connecting said at least two elastic bands.

2. An elastic pain blocking bandage comprising:
   a) an elastic band stack having at least two elastic bands stacked one atop another, having a first end and a second end and having a first side and a second side;
   b) a hook and loop fastener having:
      1) a hook portion attached to said first end of said elastic band stack and on said first side of said elastic band stack, and,
      2) a loop portion attached to said second end of said elastic band stack and on said second side of said elastic band stack; and,
   c) at least one reinforcing rib means, each of said reinforcing rib means connecting said at least two elastic bands together between said first end and said second end of said elastic band stack and extending across the width of said elastic band stack.

3. The elastic pain blocking bandage according to claim 2 wherein each of said at least one reinforcing rib means is a series stitches.

4. An elastic variable tension medical device for treating painful medical conditions comprising:
   a) at least two elastic strips stacked one atop another and forming a stack of elastic strips, said stack of elastic strips having a first end and a second end and having a first side and a second side;
   b) a hook and loop fastener having,
      1) a hook portion attached to said first side of said stack of elastic strips and on said first end of said stack of elastic strips, and,
      2) a loop portion attached to said second side of said stack of elastic strips and on said second end of said stack of elastic strips; and,
   c) at least one reinforcing rib, said reinforcing rib attaching said at least two elastic strips together between said first end and said second end and extending across the width of said stack of elastic strips, and wherein said at least one reinforcing rib is a series of stitches connecting said at least two elastic strips.

5. A method for blocking pain due to certain medical conditions comprising the steps of:
   a) providing an elastic variable tension medical device, said elastic variable tension medical device comprised of an elastic band stack having at least two elastic strips stacked one on top of another, said elastic band stack having a first end and a second end, and having a first side and a second side, said elastic band stack further having a hook and loop fastener wherein a hook portion is attached to said first end of said elastic band stack and on said first side of said elastic band stack and wherein a loop portion is attached to said second end of said elastic band stack and on said second side of said elastic band stack, said elastic band stack having at least one reinforcing rib located between said first end and said second end for connecting said at least two elastic strips and extending across the width of said variable tension medical device; and, b) wrapping said elastic variable tension medical device around an appropriate body part with sufficient tension to apply pressure on a pressure point and securing said first end and said second end of said elastic variable tension medical device together using said hook and loop fastener such that pain due to certain medical conditions is blocked.

6. The method for blocking pain due to certain medical conditions according to claim 5 wherein the step of wrapping said elastic variable tension medical device around an appropriate body part with sufficient tension to relieve pain is restricted to wrapping said elastic variable tension medical device around a body part distal to a location of pain with sufficient tension to relieve pain.

7. The method for blocking pain due to certain medical conditions according to claim 5 wherein the step of wrapping said elastic variable tension medical device around an appropriate body part includes wrapping said elastic variable tension medical device around a forearm proximal to a pain in a wrist with sufficient tension to relieve pain.

8. The method for blocking pain due to certain medical conditions according to claim 5 wherein the step of wrapping said elastic variable tension medical device around an appropriate body part includes wrapping said elastic variable tension medical device around a leg distal to a pain in a knee.

9. The method for blocking pain due to certain medical conditions according to claim 5 wherein the step of wrapping said elastic variable tension medical device around an appropriate body part includes wrapping said elastic variable tension medical device around a thigh proximal to a pain in a hamstring.

10. The method for blocking pain due to certain medical conditions according to claim 5 wherein the step of wrapping said elastic variable tension medical device around an appropriate body part includes wrapping said elastic variable tension medical device around a hand proximal to pain in a hand.

11. A method of reducing joint pain comprising the steps of:

a) wrapping an elastic strip around a portion of the body distal to a joint such that all of said elastic strip is distal to a joint and with sufficient tension to relive said joint pain such that said elastic strip overlaps itself only for hook and loop portions located at opposite ends of said elastic strip; and, b) securing said hook and loop portions to each other.

12. The method of reducing joint pain according to claim 11 further including the step of, prior to wrapping an elastic strip, of positioning the elastic strip distal to a joint at least one inch.

13. The method for blocking pain due to certain medical conditions according to claim 5 wherein the step of wrapping said elastic variable tension medical device around an appropriate body part includes wrapping said elastic variable tension medical device around a forearm distal to a pain in an elbow with sufficient tension to relieve pain.

14. The method for blocking pain due to certain medical conditions according to claim 5 wherein the step of wrapping said elastic variable tension medical device around an appropriate body part includes wrapping said elastic variable tension medical device around a lower leg proximal to a pain in an ankle with sufficient tension to relieve pain.

15. The method for blocking pain due to certain medical conditions according to claim 5 wherein the step of wrapping said elastic variable tension medical device around an appropriate body part includes wrapping said elastic variable tension medical device around a head with sufficient tension to relieve head pain.

* * * * *